United States Patent
Sturtz et al.

(10) Patent No.: US 6,821,284 B2
(45) Date of Patent: Nov. 23, 2004

(54) SURGICAL CLAMP INSERTS WITH MICRO-TRACTIVE SURFACES

(75) Inventors: Karrie L. Sturtz, Campbell, CA (US); David J. Danitz, Cupertino, CA (US); June Carnegie, Sunnyvale, CA (US); Thomas L. Baughman, Burlingame, CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 18 days.

(21) Appl. No.: 10/349,871

(22) Filed: Jan. 22, 2003

(65) Prior Publication Data

US 2004/0143276 A1 Jul. 22, 2004

(51) Int. Cl.[7] ............................................... A61B 17/04
(52) U.S. Cl. ...................................... 606/151; 606/157
(58) Field of Search ......................................... 606/151

(56) References Cited

U.S. PATENT DOCUMENTS

| | | | |
|---|---|---|---|
| 2,743,726 A | 5/1956 | Grieshaber | |
| 3,101,715 A | 8/1963 | Glassman | |
| 3,503,396 A | 3/1970 | Pierie et al. | |
| 3,509,882 A | 5/1970 | Blake | |
| 3,746,002 A | 7/1973 | Haller | |
| 4,815,460 A | 3/1989 | Porat et al. | |
| 4,931,058 A | 6/1990 | Cooper | |
| 5,258,005 A | 11/1993 | Christian | |
| 5,527,340 A | 6/1996 | Vogel | |
| 5,591,182 A | 1/1997 | Johnson | |
| 5,626,607 A * | 5/1997 | Malecki et al. ............. | 606/205 |
| 5,653,720 A | 8/1997 | Johnson et al. | |
| 5,662,665 A | 9/1997 | Ludwick | |
| 5,728,121 A | 3/1998 | Bimbo et al. | |
| 5,810,881 A | 9/1998 | Hoskin et al. | |
| 5,893,878 A | 4/1999 | Pierce | |
| 6,007,552 A * | 12/1999 | Fogarty et al. ............. | 606/157 |
| 6,030,394 A * | 2/2000 | Hart ............................ | 606/151 |
| 6,077,280 A | 6/2000 | Fossum | |
| 6,099,539 A | 8/2000 | Howell et al. | |
| 6,099,550 A | 8/2000 | Yoon | |
| 6,126,671 A | 10/2000 | Richards et al. | |
| 6,206,896 B1 * | 3/2001 | Howell et al. ............... | 606/151 |
| 6,228,104 B1 | 5/2001 | Fogarty et al. | |
| 6,267,773 B1 | 7/2001 | Gadberry et al. | |
| 6,273,902 B1 | 8/2001 | Fogarty et al. | |
| 6,387,112 B1 | 5/2002 | Fogarty et al. | |

FOREIGN PATENT DOCUMENTS

| | | |
|---|---|---|
| EP | 0 451 309 A1 | 10/1991 |
| GB | 2 086 792 A | 5/1982 |
| WO | WO 99/11179 | 3/1999 |
| WO | WO 99/43261 | 9/1999 |

OTHER PUBLICATIONS

International Search Report mailed on Apr. 26, 2004, for PCT patent application No. PCT/US03/40553, filed on Dec. 19, 2003, 4 pgs.

* cited by examiner

*Primary Examiner*—Gary Jackson
(74) *Attorney, Agent, or Firm*—Morrison & Foerster LLP

(57) ABSTRACT

Inserts configured for attachment to a jaw of a jaw-type occlusion device, such as a surgical clamp or clip, and surgical clamps or clips having such jaw inserts. The inserts include a compliant cushion having a clamping surface adapted for engagement with a vessel or other body tissue, the clamping surface having a plurality of integrally-formed raised patterns extending from the surface to at most 0.010 inches. The raised patterns can be repeating and uniform in nature, or random and non-uniform in nature.

28 Claims, 7 Drawing Sheets

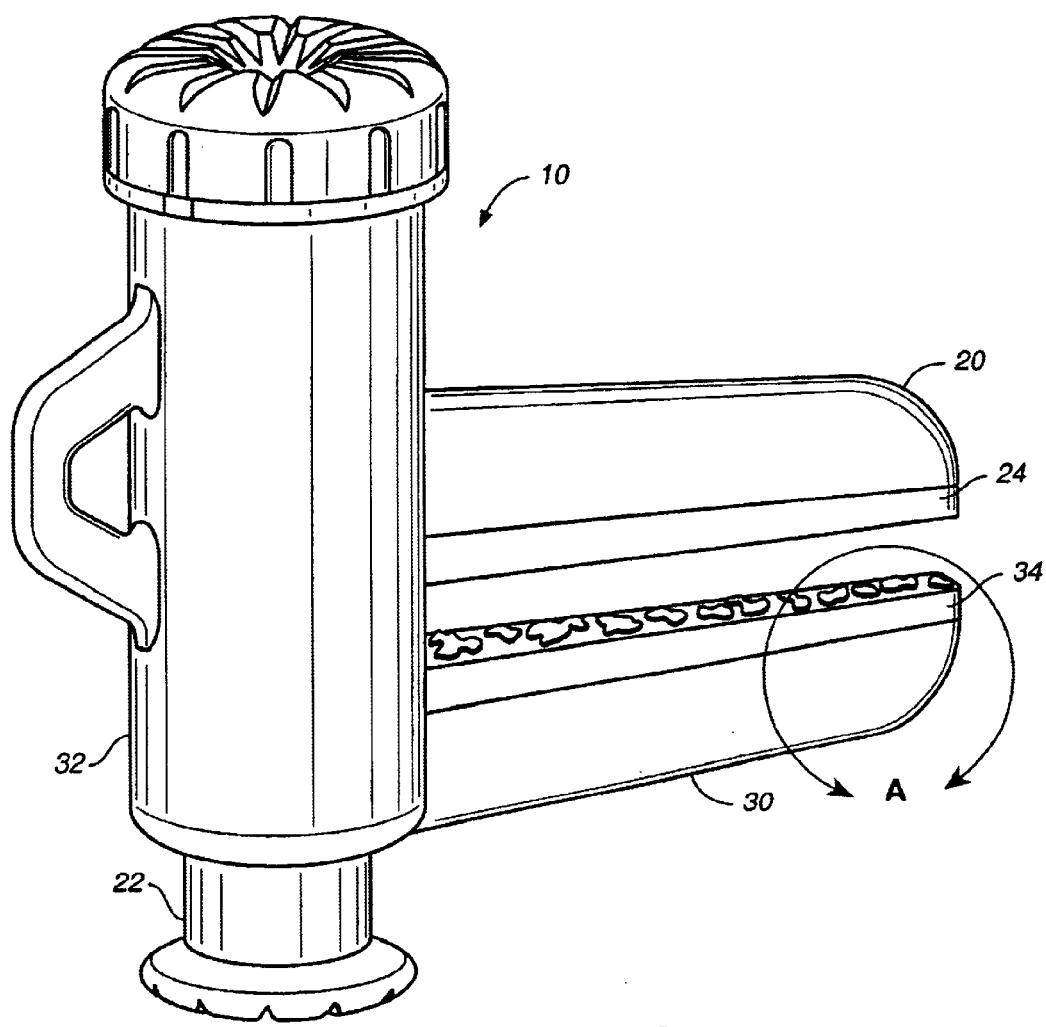
FIG._1

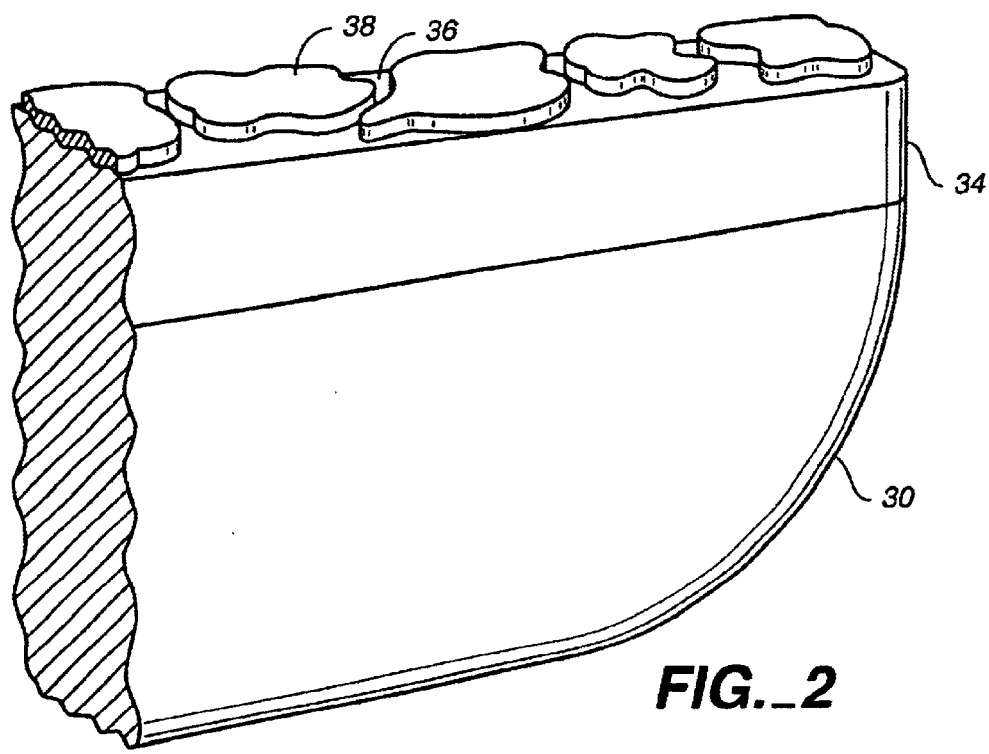
FIG._2
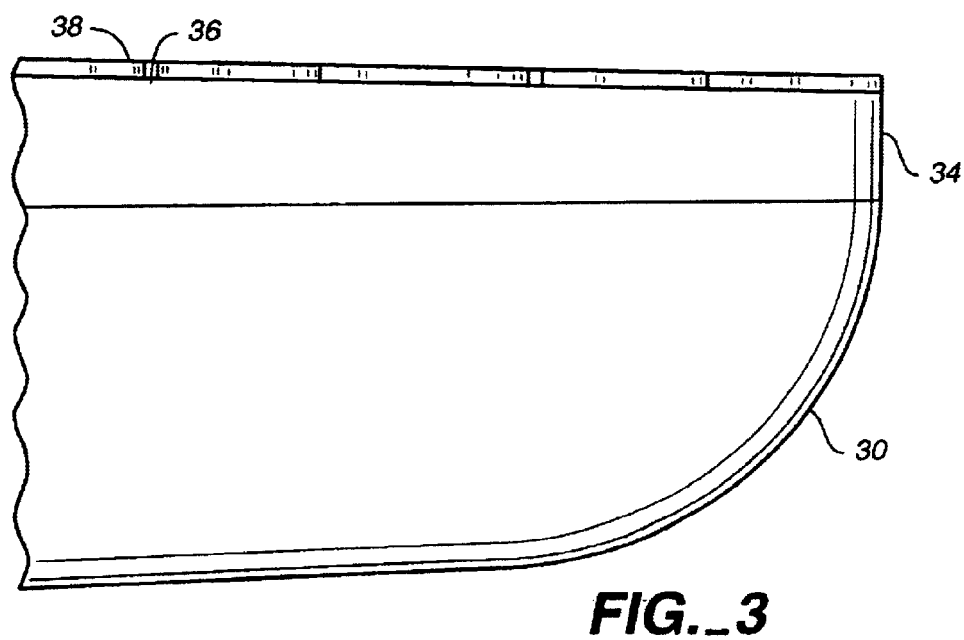
FIG._3

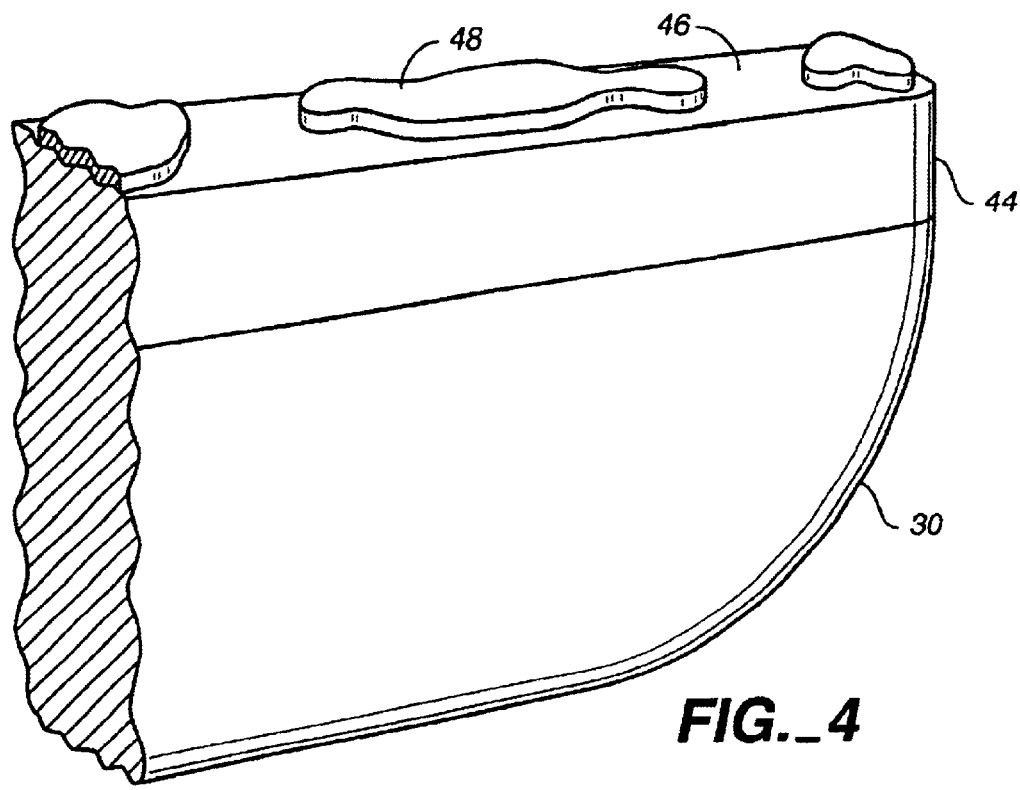
FIG._4
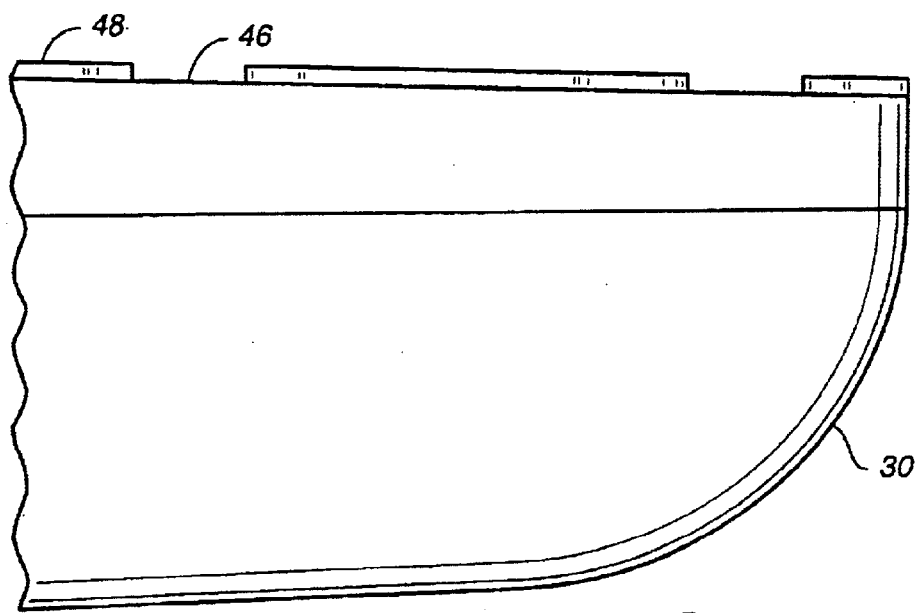
FIG._5

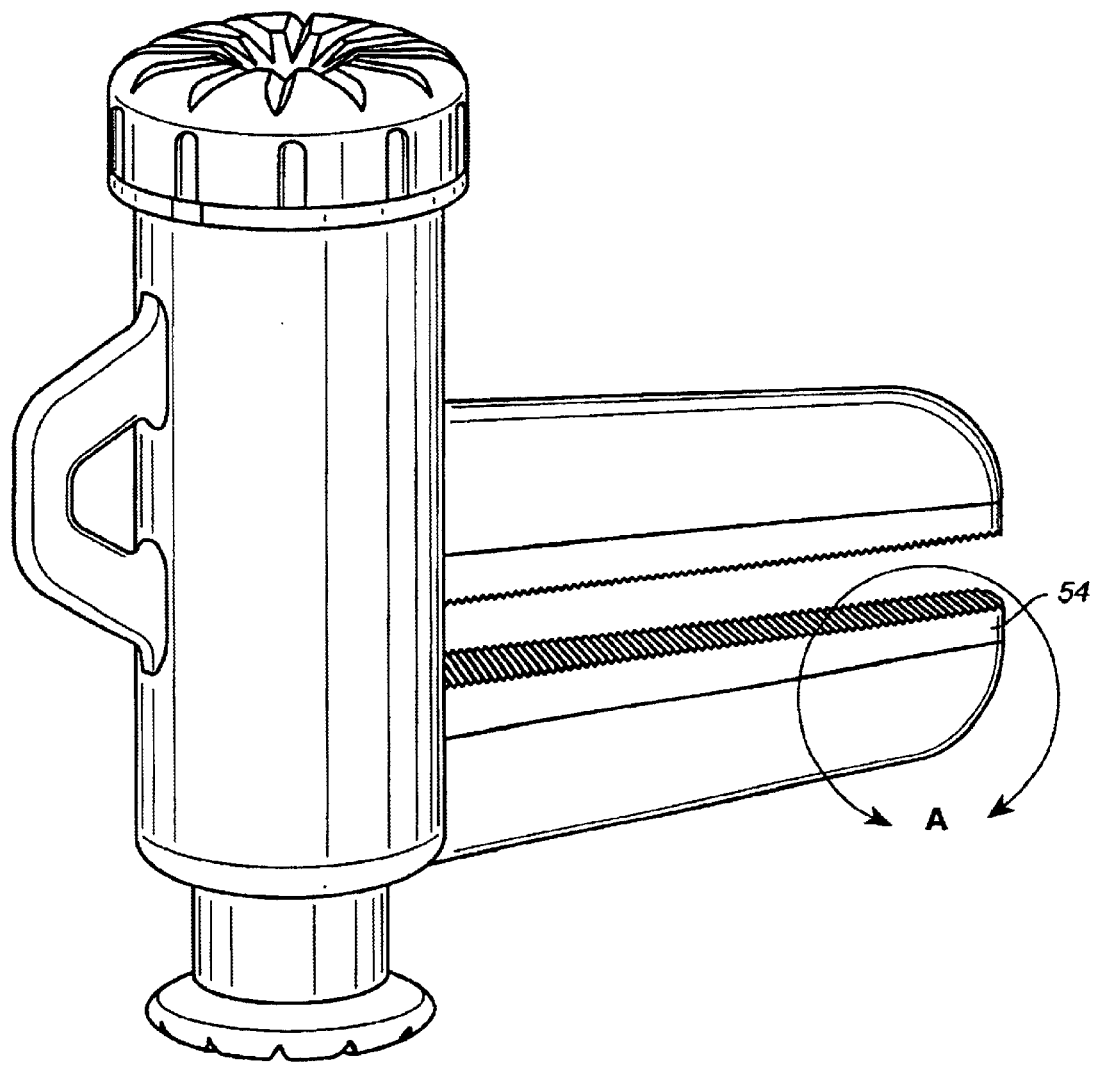
FIG._6

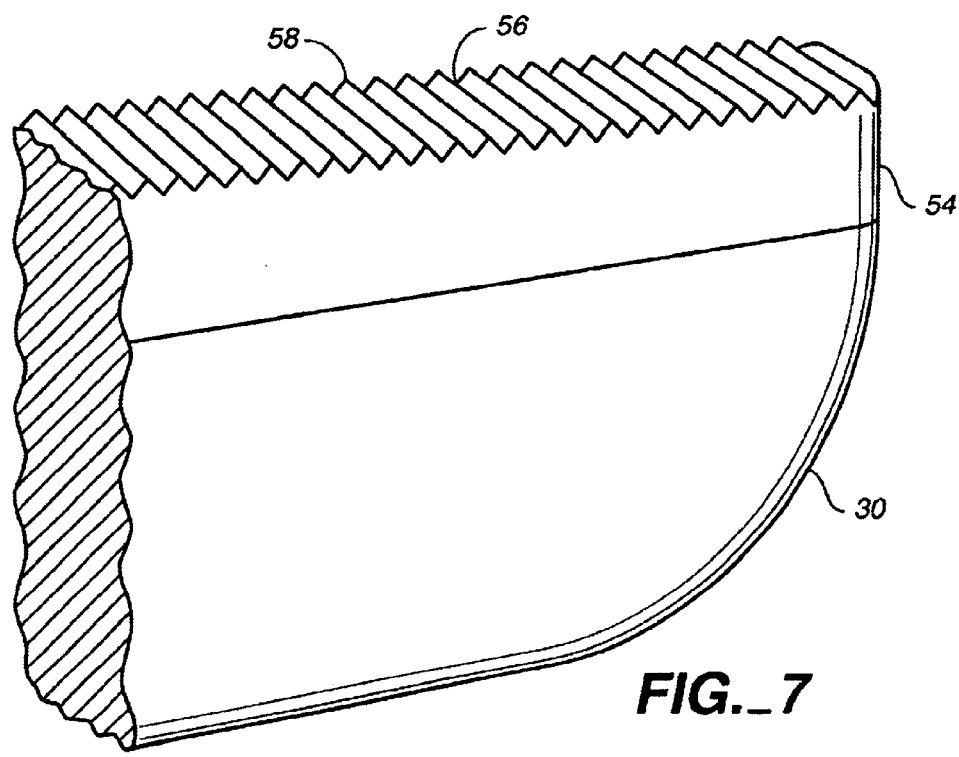
FIG._7
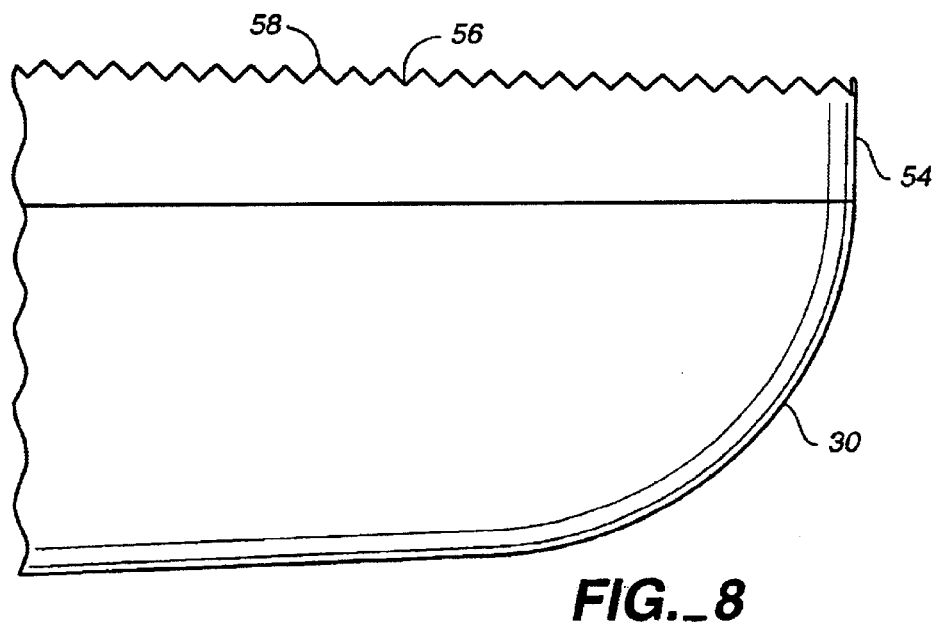
FIG._8

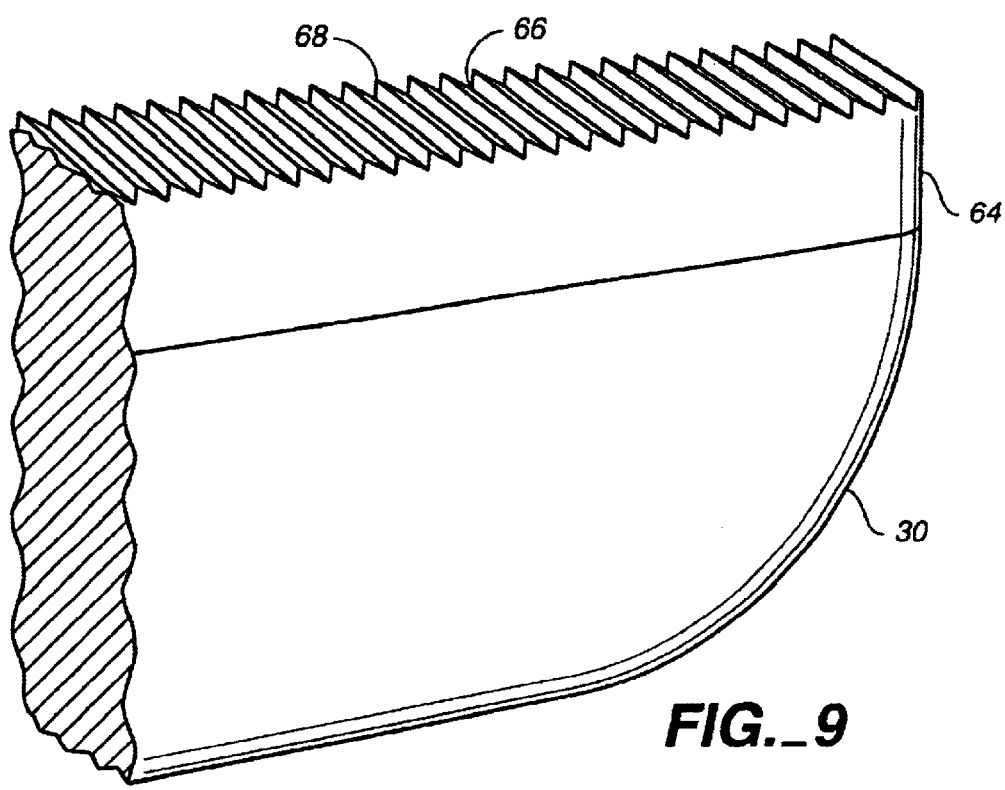
FIG._9
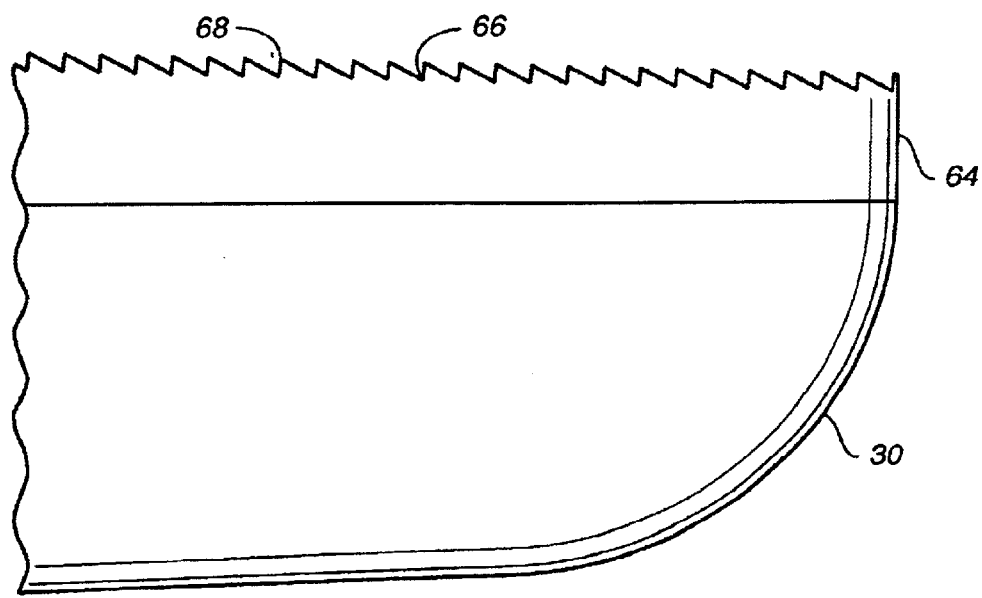
FIG._10

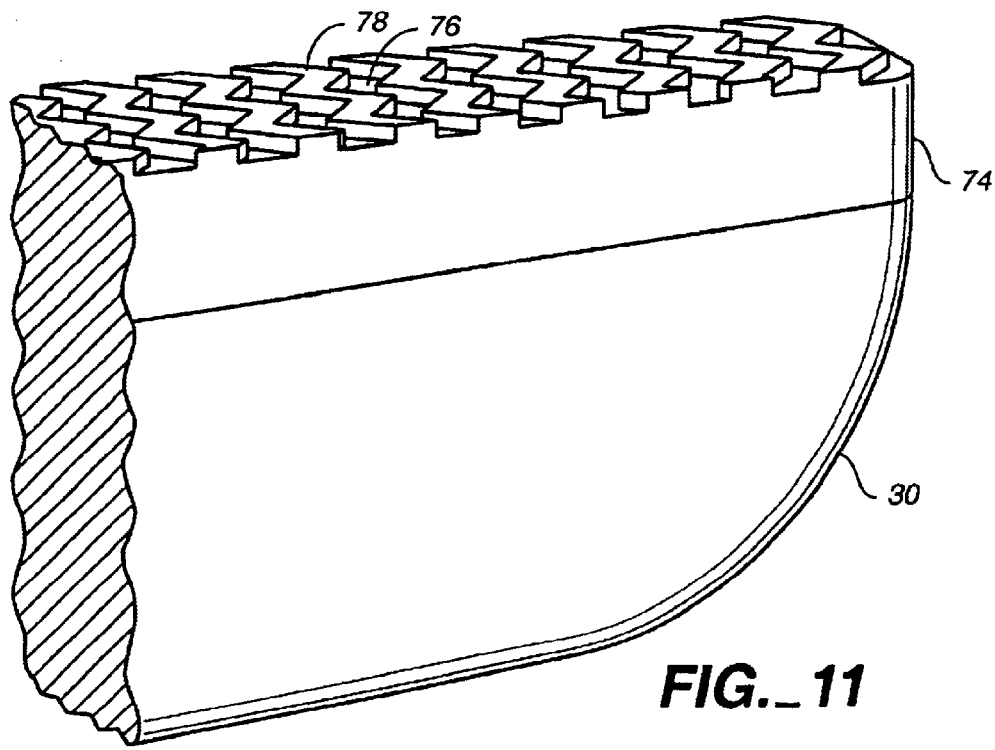
FIG._11
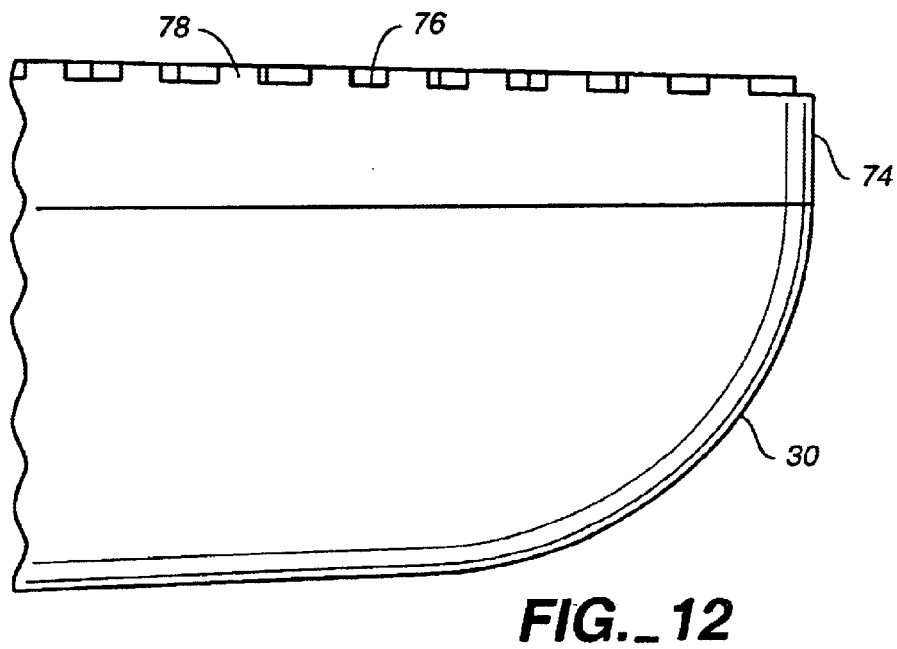
FIG._12

SURGICAL CLAMP INSERTS WITH MICRO-TRACTIVE SURFACES

BACKGROUND OF THE INVENTION

The present invention relates to surgical instruments for occluding a blood vessel or other body conduit, including jaw-type occlusion instruments such as surgical clamps and clips, and more particularly to cushioned pads, members or inserts that attach to the jaws of such clips or clamps for engagement with the target vessel or body conduit.

Instruments for occluding blood vessels and other body conduits, including jaw-type occlusion instruments, are well-known. In particular, surgical clamps commonly used for occlusion typically include pivoting jaw members that are moveable toward one another and which are actuated by handle members extending from the jaw members. The handle members typically include a ratchet mechanism to hold the engaged clamp in place. Surgical clips are commonly used to occlude smaller blood vessels and other body conduits during surgical procedures. A common type of surgical clip is the parallel jaw clip that includes a pair of jaws oriented generally parallel to one another and moveable from an open to a closed position. Many such clips include compression or extension springs for biasing the jaws together in the closed position. Representative of such clips are those described in, e.g., U.S. Pat. Nos. 3,509,882, 4,931,058, 5,653,720 and 6,267,773. Such clips have gained wide acceptance and are easy to place and remove, and provide for dependable occlusion, and are also useful for other applications, such as suture tags and identification markers.

Many conventional surgical clamps and clips are made of metal, such as stainless steel, hard plastic, or other similarly rigid materials. Such surgical clamps and clips are favored for a number of reasons. They can be manufactured to have a low profile, and the overall structural rigidity of the clamps or clips together with non-deflectable and non-deformable gripping surfaces provides for clamps and clips having good gripping properties. A disadvantage of such clamps and clips is that the hard surfaces and rigidity of the clamps can cause trauma to the clamped vessel at the site of occlusion.

As a result, a number of a traumatic versions of surgical clamps and clips have been developed for reducing trauma to a vessel during occlusion. In particular, such clamps and clips have been adapted to include jaw surfaces containing cushioned pads, members or inserts. In some cases these pads, members or inserts are prone to slipping off the clamped vessel, especially where the clamps or clips are engaged near the distal ends of their jaws. Also, due to the deformability of such pads, members or inserts, they likewise can be prone to slipping laterally along a clamped vessel, which can further result in a scissoring effect where the jaws twist off-line. In all such situations, effective clamping is compromised.

Efforts to improve a traumatic occlusion have included attempts to improve the tractive properties of the jaw inserts. These efforts include, for example, the provision of patterns of uniform raised protrusions, such as is disclosed in U.S. Pat. No. 6,099,539. Other efforts include, e.g., the provision of inserts formed of multi-composite materials. An example of such inserts include those disclosed in PCT Publication WO 99/11179 which consist of a compliant cushion covered with a mesh surface overlay.

There remains a need for a traumatic surgical clamps, clips, and accompanying jaw inserts that provide for improved gripping capabilities while minimizing trauma to an occluded vessel.

BRIEF SUMMARY OF THE INVENTION

The present invention meets these and other needs and provides for jaw inserts for attachment to the jaws of jaw-type occlusion devices, such as surgical clamps and clips.

The invention resides in part on the surprising discovery that integrally formed raised patterns that extend only incrementally from the surface of a cushioned insert provide advantageous gripping traction while minimizing trauma to the gripped vessel. The raised patterns can extend as little as 0.006 to 0.010 inches from the gripping surface, significantly less than is typically found in conventional integrally formed inserts.

In one aspect of the invention, an insert is provided that includes a compliant cushion having a clamping surface adapted for engagement with a vessel or other body tissue. The clamping surface includes a plurality of integrally-formed raised patterns extending from the surface. The raised patterns are further characterized in that they are random and non-uniform in nature. In one variation of the invention, the raised patterns cover between approximately 40% to 70% of the total clamping surface of the insert. In another variation of the invention, the raised patterns extend approximately 0.006 to 0.010 inches from the clamping surface.

In another aspect of the invention, an insert is provided that includes a compliant cushion having a clamping surface adapted for engagement with a vessel or other body tissue. The clamping surface includes a plurality of uniform integrally-formed raised patterns extending from the surface extending approximately 0.006 to 0.010 inches from the clamping surface. In one variation, the raised patterns are a series of teeth-like ridges extending across the width of the cushion surface. In a further variation, the ridges are further formed such that the ridge faces directed toward the proximal end of the insert are perpendicular to the cushion surface, whereas the ridge faces directed toward the distal end of the insert are sloped. Such a design further discourages migration of clamped vessel toward the distal end of the insert. In another variation, the raised patterns are a series of repeating chevron patterns, also extending across the width of the cushion. In certain variations, the ridges or chevron patterns have an individual width of approximately 0.010 inches.

In further aspects of the invention, the inserts are configured for attachment to a surgical clamp or a surgical clip.

In yet further aspects of the invention, surgical clamps or clips are provided having at least one jaw having a compliant cushion having a clamping surface adapted for engagement with a vessel or other body tissue. The clamping surface includes a plurality of integrally-formed raised patterns extending from the surface.

The invention and its advantages will be even more apparent in view on the following description and accompanying drawings.

BRIEF DESCRIPTION OF THE DRAWINGS

FIG. 1 illustrates a perspective view of a surgical clip having a jaw with a cushioned clamping surface according to one variation of the invention;

FIG. 2 is an enlarged view of the jaw and clamping surface of FIG. 1, with parts broken away;

FIG. 3 is a side view of the jaw and clamping surface of FIG. 2;

FIG. 4 illustrates a perspective view of a surgical clip jaw with a cushioned clamping surface according to another variation of the invention, with parts broken away;

FIG. 5 is a side view of the jaw and clamping surface of FIG. 4;

FIG. 6 illustrates a perspective view of a surgical clip having a jaw with a cushioned clamping surface according to yet another variation of the invention;

FIG. 7 is an enlarged view of the jaw and clamping surface of FIG. 6, with parts broken away;

FIG. 8 is a side view of the jaw and clamping surface of FIG. 7;

FIG. 9 illustrates a perspective view of a surgical clip jaw with a cushioned clamping surface according to a further variation of the invention, with parts broken away;

FIG. 10 is a side view of the jaw and clamping surface of FIG. 9;

FIG. 11 illustrates a perspective view of a surgical clip jaw with a cushioned clamping surface according to yet another variation of the invention, with parts broken away;

FIG. 12 is a side view of the jaw and clamping surface of FIG. 10;

DETAILED DESCRIPTION OF THE INVENTION

A surgical clip according to one aspect of the present invention is depicted in FIGS. 1–3. Surgical clip 10 contains features of conventional parallel jaw clips including opposing upper and lower jaws 20 and 30, respectively, that extend from upper and lower barrels 22 and 32 respectively. The barrels are arranged in a telescoping relationship, and a biasing means such as a compression spring (not shown) is located within the barrels. The biasing means urges the jaws together to clamp or otherwise engage a blood vessel, body conduit, or other tissue positioned between the jaws. Upper and lower jaws 20 and 30, include in particular cushioned jaw inserts 24 or 34, respectively, that are the subject of the present invention. As used herein, the term "insert" refers to a pad or cushion attached to, or configured for attachment to, a surgical clip or clamp jaw surface.

As shown more clearly in FIGS. 2–3, insert 34 includes a clamping surface 36 oriented and adapted for engaging vessel, body conduit, or other tissue. Surface 36 includes a plurality of raised patterns 38 extending upward from the surface. As can be seen, the various raised patterns are of a variety of different, arbitrary shapes such that, as a whole, the raised patterns are random and nonuniform in nature. The raised patterns 38 of insert 34 cover approximately 70% of the total clamping surface 36 of the insert, and extend from the clamping surface approximately 0.010 inches.

FIGS. 4–5 show a variation on clamping surface 36. In this variation, insert 44 likewise includes a plurality of integrally formed raised patterns 48 extending from the clamping surface 46. Again these raised patterns are random and nonuniform in nature. In this variation, the patterns extend over approximately 40% of the total clamping surface of the insert and extend from the clamping surface approximately 0.006 inches.

FIGS. 6 shows a surgical clip according to another aspect of the invention. In this aspect, insert 54 includes a plurality of integrally formed raised patterns 58 extending from clamping surface 56. As more clearly seen in FIGS. 7–8, these raised patterns are a series of uniform, repeating teeth-like ridges that extend across the width of the clamping surface, each ridge being approximately 0.007 inches in height and approximately 0.010 inches in width, with the apex of the ridge oriented generally in the midpoint of the ridge. FIGS. 9–10 show a variation on clamping surface 56. In this variation, insert 64 likewise includes a series of uniform, repeating teeth-like ridges 68 extending across the width of surface 66. However, in this variation, the ridges are formed such that the slope of each ridge facing toward the proximal end of the insert is oriented perpendicular to the cushion surface, with a gradual slope on the side facing toward the distal end of the insert.

FIGS. 11–12 show yet another variation on clamping surface 56. In this variation, insert 74 again includes a series of uniform, repeating raised patterns 78 extending from the clamping surface 76. As shown, the raised patterns have a generally flat surface and constant width, and extend across the width of surface 76 in a chevron design. Each raised pattern extends 0.009 inches upward from surface 76 and is 0.010 inches in width.

The inventors have surprisingly found that inserts having these features provide for better traction as compared to smooth surfaced inserts and comparable, and in some cases superior, traction capabilities as compared to other textured jaw inserts. The good traction afforded by inserts with these features is also surprising given that the height of the raised surfaces is fairly minimal, i.e., 0.006–0.010 inches. This is ten-fold less or more than many other known inserts, which have e.g. raised protrusion height of 0.150 inches or more, such as e.g. those disclosed in U.S. Pat. No. 6,099,539. In addition, and as further detailed herein, in many cases these inserts leave reduced or lessened imprints, or "witness marks," on a clamped vessel post-deployment, as compared to conventional atraumatic clips having jaw inserts with e.g. multi-composite or repeating patterned surfaces. It is believed that lessened or reduced residual witness marks corresponds to less trauma to the clamped vessel.

Inserts according to the invention can be formed of a variety of materials known in the art that are compliant and that will thus provide a cushioning effect to the clamped vessel, body conduit or other tissue. Most suitable are elastomeric materials that are resiliently deflectable. Such elastomeric materials include, but are not limited to, natural rubber, neoprene, urethane, ethel vinyl acetate foam, or silicon, or silicon foam. It is desirable that the material be a thermoplastic elastomer suitable for injection molding and having a 20A to 40A shore durometer rating. Such thermoplastic elastomers include polyurethane and thermoplastic elastomers sold under the trade KRATON™ and DYNAFLEX™ (Shell Chemicals Ltd.). By injection molding the insert, the raised surface patterns, e.g., 38, 48, 58, 68, 78, can thus be integrally formed with the insert itself. Such inserts can further be insert molded directly on to jaws of a surgical clip, or can otherwise be affixed to the jaws using mechanical bonding, adhesives, or other known means.

While inserts have been described above with relation to a surgical clip, it is also contemplated that inserts according to the present invention can likewise be configured for attachment or securement to larger surgical clamps. Such inserts can be permanently affixed to the jaws of such clamps, or can otherwise be configured for removable engagement with the jaws of such clamps. For example, the insert can be overmolded on to or otherwise affixed to an attachment member providing a rigid backing for the cushion as well as means for attaching the insert to the jaw of the clamp. Such an attachment member (not shown) can be made of a hard plastic, such as polycarbonate, or of metal.

The means for attachment can include, for example, protrusions, tabs, or other similar extensions, that are configured for detachable engagement with correspondingly configured recesses on the jaw itself.

Alternatively, the insert can be secured to a clamp jaw by means described in U.S. Pat. Nos. 6,228,104, 6,273,902, and 6,387,112, each commonly owned by the assignee of the present application and incorporated herein in its entirety. Briefly, such means include a flexible elongate attachment member configured to be received in elongate cavity or channel that extends longitudinally of a clamped jaw. Such attachment members can be formed of a plastic that is flexible but generally stiffer and markedly less deflectable than the insert material. Suitable materials include nylon or polypropylene. Such a design is especially advantageous in that the resulting insert can accommodate a variety of jaw shapes and configurations, including curved jaws.

The invention will be better understood by reference to the following illustrative examples, which are offered by way of illustration only and not by way of limitation.

EXAMPLES

Surgical clips containing jaw inserts according to the present invention were tested against existing conventional clips with respect to traction capabilities and the ability to minimize vessel witness marks left by the clip post-placement. The clips were applied to a porcine carotid vessel that was pressurized to a blood pressure of 120 mmHg. The vessel was submersed in whole milk at room temperature to lubricate the vessel, in order to simulate surgical conditions in which blood vessels are typically coated on their outer surfaces by blood in the surgical field. Previous studies indicate that porcine carotid vessels lubricated with whole milk closely match the physical properties of human cadaver vessels lubricated with actual blood. This system is thus a close approximation of actual surgical conditions. In each case, the tested clip was applied to the vessel thereby occluding the vessel.

The clamping force exerted by each tested clip ranged from 0.50 to 1.0 pounds of clamping force. More specifically, clips were tested at clamping forces of 0.85–1.00 lbs. (full force), 0.70–0.85 lbs. (¾ force), and 0.50–0.65 lbs. (½ force). The attached clips were each subjected to force in both the horizontal (or lateral) direction and in the vertical (or axial) direction. More specifically, each clip was pulled either laterally off the vessel (i.e. horizontal pull test) or axially along the vessel (i.e. vertical pull test) at a constant speed, and the maximum force exerted on the clip during the process was recorded. The maximum force exerted is considered indicative of the tractive force applied by the jaw clamping surfaces to the engaged vessel.

The following surgical clips were tested:

Fogarty Softjaw. Fogarty Softjaw™ Spring Clip (Model No. CSOFT6, Edwards Life Sciences, Irvine, Calif.) includes natural sponge rubber inserts with a smooth surface. An interior cavity runs the length of the inserts.

Novare Surgical Greyhound. Greyhound™ Adjustable Spring Clip (Item No. N-10157, Novare Surgical Systems, Cupertino, Calif.) contains smooth soft jaw surfaces formed of an elastomer.

Applied Medical Standard. Standard Surgical Clip (Applied Medical, Rancho Santa Margarita, Calif., Model No. AVD-6025) contains soft jaw inserts having series of repeating ridges with dimensions of 0.040 inches width by 0.020 inches height.

Applied Medical Fibra. Fibra® surgical clips (Applied Medical, Rancho Santa Margarita, Calif., Model No. G-6050) include soft jaw inserts of foam overlaid with a woven layer containing nylon projections that interact and engage with vessel adventitia much like Velcro hooks and loops.

Applied Medical Stealth. Stealth™ surgical spring clips (Applied Medical, Rancho Santa Margarita, Calif., Model No. A1601) include soft jaw inserts encased in mesh.

Wedge and Groove. A surgical clip was prepared having soft jaw inserts with a repeating "wedge and groove" pattern generally according to that as described in U.S. Pat. No. 6,099,539, incorporated herein by reference in its entirety. The inserts were formed of an elastomer and the raised wedges of the pattern had dimensions of 0.060 inches width by 0.060 inches height.

Microsandpaper. A surgical clip was prepared according to the embodiments of FIGS. 1–3 above. The jaw inserts were formed of an elastomer and included integrally formed raised patterns that are random and nonuniform in nature, and that extend to a height of approximately 0.010 inches and which cover approximately 70% of the total jaw surface.

Microskin. A surgical clip was prepared according to the embodiment of FIGS. 4–5. The jaw inserts were formed of an elastomer and include raised patterns that are random and nonuniform in nature, and that extend to a height of approximately 0.006 inches and that cover approximately 40% of the total jaw surface.

Microramps. A surgical clip was prepared according to the embodiment of FIGS. 6–8 having jaw inserts formed of an elastomer. The jaw inserts include integrally formed, repeating ridges extending across the width of the surface, the ridges being approximately 0.007 inches high and 0.010 wide.

Microchevron. A surgical clip was prepared according to the embodiment of FIGS. 11–12 having jaw inserts formed of an elastomer. The jaw inserts include integrally formed raised patterns in a chevron design extending across the width of the insert, each having a height of 0.009 inches and a width of 0.010 inches.

The results of the horizontal and vertical pull tests are indicated in Tables I and II below.

TABLE I

| | Horizontal Pull Test | | | | |
| --- | --- | --- | --- | --- | --- |
| | Clamping Force (lbs.) | | | | Max. |
| Clip | Full | 3/4 | 1/2 | 1/4 | Force (lbs.) |
| Fogarty Softjaw | X | | | | 0.21 |
| Novare Greyhound | X | | | | 0.16 |
| Applied Standard | X | | | | 0.42 |
| Applied Fibra | X | | | | 0.21 |
| Wedge & Groove | X | | | | 0.21 |
| Microsandpaper | X | | | | 0.51 |
| Microskin | X | | | | 0.35 |
| Microramps | X | | | | 0.55 |
| Microchevrons | X | | | | 0.48 |
| Applied Standard | | X | | | 0.21 |

TABLE I-continued

Horizontal Pull Test

| Clip | Clamping Force (lbs.) | | | | Max. Force (lbs.) |
|---|---|---|---|---|---|
| | Full | 3/4 | 1/2 | 1/4 | |
| Micro-sandpaper | | X | | | 0.26 |
| Microskin | | X | | | 0.17 |
| Microramps | | X | | | 0.43 |
| Micro-chevrons | | X | | | 0.38 |
| Applied Stealth | | | X | | 0.69 |
| Micro-sandpaper | | | X | | 0.22 |
| Microskin | | | X | | 0.18 |
| Microramps | | | X | | 0.43 |
| Micro-chevrons | | | X | | 0.36 |

TABLE II

Vertical Pull Test

| Clip | Clamping Force (lbs.) | | | | Max. Force (lbs.) |
|---|---|---|---|---|---|
| | Full | 3/4 | 1/2 | 1/4 | |
| Fogarty Softjaw | X | | | | 0.62 |
| Novare Greyhound | X | | | | 0.58 |
| Applied Standard | X | | | | 0.83 |
| Applied Fibra | X | | | | 0.80 |
| Wedge & Groove | X | | | | 0.59 |
| Micro-sandpaper | X | | | | 1.12 |
| Microskin | X | | | | 0.49 |
| Microramps | X | | | | 1.32 |
| Micro-chevrons | X | | | | 0.94 |
| Applied Standard | | X | | | 0.36 |
| Micro-sandpaper | | X | | | 0.74 |
| Microskin | | X | | | 0.70 |
| Microramps | | X | | | 0.97 |
| Micro-chevrons | | X | | | 0.89 |
| Applied Stealth | | | X | | 0.97 |
| Micro-sandpaper | | | X | | 0.67 |
| Microskin | | | X | | 0.70 |
| Microramps | | | X | | 0.91 |
| Micro-chevrons | | | X | | 0.79 |

The results of both these tests indicate that the clips with inserts of the present invention perform as well as, if not better than, currently marketed clips, and other insert surfaces having repeating patterns of larger, uniform protrusions.

Next, each tested clip above was applied to a new porcine carotid vessel under similar conditions, and allowed to remain clamped on the vessel for 20 minutes. The clips were then removed, and the vessel was visually examined for the level and degree of imprints or marks left on the outside of the vessel as a result of application of the clip (i.e. so-called "witness marks"). Deep and pervasive imprints are considered to be traumatic to the vessel and/or potentially damaging to the vessel. Therefore, minimizing the imprint left by a pad surface minimizes potential damage to the vessel. From visual observations, the witness marks left by clips with inserts of the present invention, especially the inserts with the random, nonuniform, and noncontiguous patterns, were the least visible, giving an indication that these inserts are the least traumatic of the tested clips. The Applied Medical and Fogarty clips, by contrast, gave the deepest marks and impressions and thus can be considered more detrimental. There were no apparent witness marks left on the interior of the vessel with respect to any of the tested clips.

Although only certain embodiments have been illustrated and described, those having ordinary skill in the art will understand that the invention is not intended to be limited to the specifics of any of these embodiments but rather is defined by the accompanying claims.

We claim:

1. An insert for attachment to a jaw of a jaw-type occlusion device comprising a compliant cushion having a clamping surface adapted for engagement with a vessel or other body tissue, the clamping surface having a plurality of integrally-formed raised patterns extending from the surface, the raised patterns being random and non-uniform in nature.

2. The insert of claim 1 wherein the raised patterns cover between approximately 40% to 70% of total clamping surface of the insert.

3. The insert of claim 1 wherein the raised patterns extend approximately 0.006 to 0.010 inches from clamping surface.

4. The insert of claim 1 wherein the insert is further configured for attachment to a surgical clip.

5. The insert of claim 1 wherein the insert is further configured for attachment to a surgical clamp.

6. A surgical clip comprising at least one jaw having a compliant clamping surface adapted for engagement with a vessel or other body tissue, the clamping surface having a plurality of integrally-formed raised patterns extending from the surface, the raised patterns being random and non-uniform in nature.

7. The surgical clip of claim 6 wherein the raised patterns cover between approximately 40% to 70% of total clamping surface of the jaw.

8. The surgical clip of claim 6 wherein the raised patterns extend approximately 0.006 to 0.010 inches from clamping surface of the jaw.

9. A surgical clamp comprising at least one jaw having a compliant clamping surface adapted for engagement with a vessel or other body tissue, the clamping surface having a plurality of integrally-formed raised patterns extending from the surface, the raised patterns being random and non-uniform in nature.

10. The surgical clamp of claim 9 wherein the raised patterns cover between approximately 40% to 70% of total clamping surface of the jaw.

11. The surgical clamp of claim 9 wherein the raised patterns extend approximately 0.006 to 0.010 inches from clamping surface of the jaw.

12. An insert for attachment to a jaw of a jaw-type occlusion device comprising a compliant cushion having a clamping surface adapted for engagement with a vessel or other body tissue, the clamping surface having a plurality of uniform, integrally-formed raised patterns extending approximately 0.006–0.010 inches from the surface.

13. The insert of claim 12 wherein the uniform raised patterns have widths of approximately 0.010 inches.

14. The insert of claim 12 wherein the uniform raised patterns further comprise teeth-like ridges extending across the width of the cushion surface.

15. The insert of claim 14 wherein the proximal-facing slopes of the teeth-like ridges are generally perpendicular to the surface.

16. The insert of claim 12 wherein the uniform raised patterns further comprise chevron-like patterns extending across the width of the cushion surface.

17. The insert of claim 12 wherein the insert is further configured for attachment to a surgical clip.

18. The insert of claim 12 wherein the insert is further configured for attachment to a surgical clamp.

19. A surgical clip comprising at least one jaw having a compliant cushion having a clamping surface adapted for engagement with a vessel or other body tissue, the clamping surface having a plurality of uniform, integrally-formed raised patterns extending approximately 0.006–0.010 inches from the surface.

20. The surgical clip of claim 19 wherein the uniform raised patterns have widths of approximately 0.010 inches.

21. The surgical clip of claim 19 wherein the uniform raised patterns further comprise teeth-like ridges extending across the width of the cushion surface.

22. The surgical clip of claim 21 wherein the proximal-facing slopes of the teeth-like ridges are generally perpendicular to the surface.

23. The surgical clip of claim 19 wherein the uniform raised patterns further comprise chevron-like patterns extending across the width of the cushion surface.

24. A surgical clamp comprising at least one jaw having a compliant clamping surface adapted for engagement with a vessel or other body tissue, the clamping surface having a plurality of uniform, integrally-formed raised patterns extending approximately 0.006–0.010 inches from the surface.

25. The surgical clamp of claim 24 wherein the uniform raised patterns have widths of approximately 0.010 inches.

26. The surgical clamp of claim 24 wherein the uniform raised patterns further comprise teeth-like ridges extending across the width of the cushion surface.

27. The surgical clamp of claim 26 wherein the proximal-facing slopes of the teeth-like ridges are generally perpendicular to the surface.

28. The surgical clamp of claim 24 wherein the uniform raised patterns further comprise chevron-like patterns extending across the width of the cushion surface.

* * * * *